United States Patent
Kalidindi et al.

(10) Patent No.: US 8,925,026 B2
(45) Date of Patent: Dec. 30, 2014

(54) BACK OFFICE SUPPORT FOR A VIDEO PROVISIONING SYSTEM

(75) Inventors: Srirama R. Kalidindi, Flower Mound, TX (US); Sanjay Ahuja, Irving, TX (US)

(73) Assignee: Verizon Patent and Licensing Inc., Basking Ridge, NJ (US)

(*) Notice: Subject to any disclaimer, the term of this patent is extended or adjusted under 35 U.S.C. 154(b) by 223 days.

(21) Appl. No.: 13/196,744

(22) Filed: Aug. 2, 2011

(65) Prior Publication Data
US 2012/0079524 A1 Mar. 29, 2012

Related U.S. Application Data

(60) Provisional application No. 61/387,939, filed on Sep. 29, 2010.

(51) Int. Cl.
| | |
|---|---|
| *H04N 7/173* | (2011.01) |
| *H04N 7/16* | (2011.01) |
| *G06F 7/00* | (2006.01) |
| *G06F 17/00* | (2006.01) |
| *A61N 5/06* | (2006.01) |
| *H04N 21/2225* | (2011.01) |
| *H04N 21/258* | (2011.01) |
| *H04N 21/2668* | (2011.01) |
| *H04N 21/431* | (2011.01) |
| *H04N 21/472* | (2011.01) |
| *H04N 21/475* | (2011.01) |
| *H04N 21/84* | (2011.01) |
| *H04N 21/8549* | (2011.01) |

(52) U.S. Cl.
CPC .......... *A61N 5/0618* (2013.01); *H04N 21/2225* (2013.01); *H04N 21/25891* (2013.01); *H04N 21/2668* (2013.01); *H04N 21/4316* (2013.01); *H04N 21/47202* (2013.01); *H04N 21/4755* (2013.01); *H04N 21/84* (2013.01); *H04N 21/8549* (2013.01)
USPC .............. 725/115; 725/91; 707/610; 707/624

(58) Field of Classification Search
CPC .................... H04N 21/2225; H04N 21/22591; H04N 21/2668; H04N 21/4316; H04N 21/47202; H04N 21/4735; H04N 21/84; H04N 21/8549; A61N 5/0618
USPC .............. 725/86, 91, 119, 115; 707/610, 624
See application file for complete search history.

(56) References Cited

U.S. PATENT DOCUMENTS

| | | | | |
|---|---|---|---|---|
| 5,543,851 | A * | 8/1996 | Chang | 348/468 |
| 7,904,678 | B1 * | 3/2011 | Karr et al. | 711/162 |

(Continued)

*Primary Examiner* — James R Sheleheda

(57) ABSTRACT

A system may receive, from a set top box (STB), a request for a video asset; retrieve a profile, associated with a user of the STB, that identifies a device, associated with the user, that is a different type of device than the STB; determine whether a transaction history associated with the STB or another transaction history, associated with the device, indicates that the video asset is authorized to be transmitted to the STB; transmit the video asset to the STB based on a determination that the transaction history or the other transaction history indicates that the video asset is authorized to be transmitted to the STB; perform a transaction on the video asset based on a determination that the first transaction history or the second transaction history does not indicate that the video asset is authorized be transmitted to the STB, and transmit the video asset to the STB as a result of the transaction.

23 Claims, 9 Drawing Sheets

(56) References Cited

U.S. PATENT DOCUMENTS

| | | | |
|---|---|---|---|
| 8,019,722 B2* | 9/2011 | Linkert et al. | 707/617 |
| 8,261,307 B1* | 9/2012 | Islam et al. | 725/62 |
| 8,707,378 B2* | 4/2014 | Nambakkam et al. | 725/115 |
| 2002/0133830 A1* | 9/2002 | Kim et al. | 725/142 |
| 2005/0071280 A1* | 3/2005 | Irwin et al. | 705/59 |
| 2005/0278760 A1* | 12/2005 | Dewar et al. | 725/94 |
| 2007/0124309 A1* | 5/2007 | Takase et al. | 707/10 |
| 2007/0239864 A1* | 10/2007 | Kwon et al. | 709/223 |
| 2007/0276983 A1* | 11/2007 | Zohar et al. | 711/100 |
| 2008/0276278 A1* | 11/2008 | Krieger et al. | 725/40 |
| 2008/0320543 A1* | 12/2008 | Wang et al. | 725/131 |
| 2009/0019492 A1* | 1/2009 | Grasset | 725/45 |
| 2009/0164790 A1* | 6/2009 | Pogodin | 713/176 |
| 2009/0262741 A1* | 10/2009 | Jungck et al. | 370/392 |
| 2010/0036748 A1* | 2/2010 | Siegel et al. | 705/26 |
| 2010/0106684 A1* | 4/2010 | Pizzo et al. | 707/610 |
| 2010/0146567 A1* | 6/2010 | Mehta et al. | 725/91 |
| 2010/0153334 A1* | 6/2010 | Takemura et al. | 707/610 |
| 2010/0161716 A1* | 6/2010 | Kajos et al. | 709/203 |
| 2010/0180308 A1* | 7/2010 | Howcroft et al. | 725/53 |
| 2010/0251280 A1* | 9/2010 | Sofos et al. | 725/14 |
| 2011/0067049 A1* | 3/2011 | Piepenbrink et al. | 725/30 |
| 2011/0106910 A1* | 5/2011 | Grasset | 709/217 |
| 2011/0119696 A1* | 5/2011 | Piepenbrink et al. | 725/23 |
| 2011/0145187 A1* | 6/2011 | Himmelsbach et al. | 707/610 |
| 2011/0161995 A1* | 6/2011 | Paul et al. | 725/5 |
| 2011/0219229 A1* | 9/2011 | Cholas et al. | 713/168 |
| 2011/0282949 A1* | 11/2011 | Rivkin | 709/206 |
| 2011/0306368 A1* | 12/2011 | McCarthy | 455/466 |
| 2012/0047539 A1* | 2/2012 | Hao et al. | 725/82 |
| 2012/0078703 A1* | 3/2012 | Berger et al. | 705/14.27 |
| 2012/0079606 A1* | 3/2012 | Evans et al. | 726/28 |
| 2012/0143997 A1* | 6/2012 | Leighton et al. | 709/219 |
| 2012/0157043 A1* | 6/2012 | LaJoie et al. | 455/407 |
| 2012/0185492 A1* | 7/2012 | Israel et al. | 707/754 |
| 2012/0284724 A1* | 11/2012 | Alexander | 718/102 |
| 2012/0295243 A1* | 11/2012 | Capone et al. | 434/362 |
| 2012/0297084 A1* | 11/2012 | Gordon | 709/233 |
| 2012/0297311 A1* | 11/2012 | Duggal | 715/740 |
| 2012/0303763 A1* | 11/2012 | Duggal | 709/219 |
| 2012/0311091 A1* | 12/2012 | Dingler et al. | 709/219 |
| 2012/0317309 A1* | 12/2012 | Benco et al. | 709/248 |

\* cited by examiner

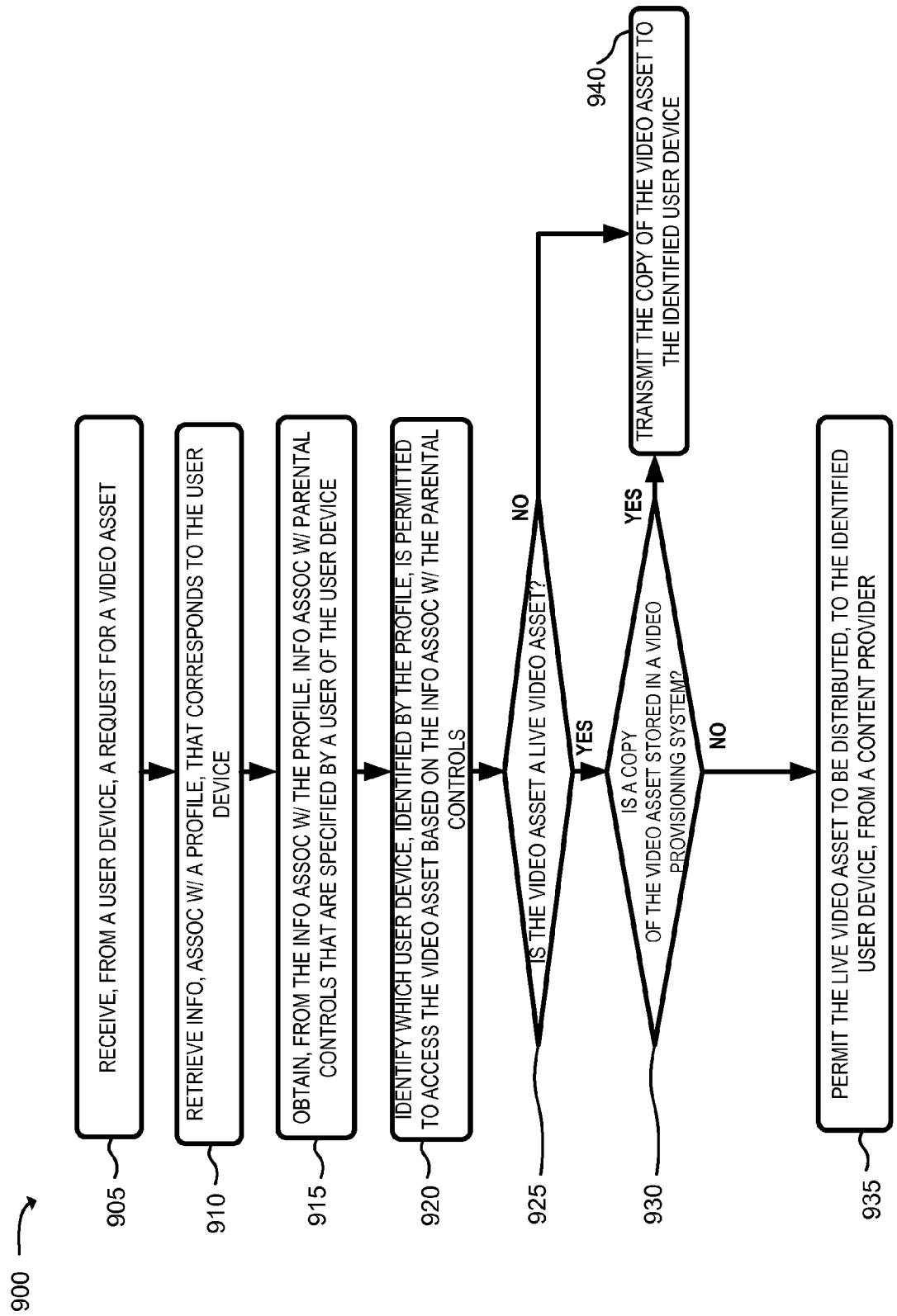

BACK OFFICE SUPPORT FOR A VIDEO PROVISIONING SYSTEM

REFERENCE TO RELATED APPLICATION

This application claims priority to U.S. Provisional Patent Application No. 61/387,939, filed Sep. 29, 2010, the entire contents of the provisional application being incorporated herein by reference.

BACKGROUND

Users, of user devices, have a growing array of sources, networks, and/or content providers from which to obtain video content and/or services. The users may use video client devices (e.g., a set top box, etc.) to obtain free broadcast television video content (e.g., from Fox, ABC, CBS, etc.), on-demand video content (e.g., Video On-Demand (VOD), pay-per-view (PPV), etc.), and/or pay television video content (e.g., from HBO, Cinemax, etc.) from cable television operators (e.g., Comcast, Time Warner, etc.) and/or satellite television operators (e.g., DirectTV, Dish Network, etc.). The users may use computer devices, wireless mobile handset devices, etc. to obtain other video content from on-line content providers, such as television operators (e.g., ABC, Fox, CBS, etc.), over-the-top (OTT) content providers (e.g., Hulu, Veoh, Jaman, YouTube, etc.), and/or other commercial content providers (e.g., Apple Computer's iTunes, Netflix, Blockbuster, etc.).

BRIEF DESCRIPTION OF THE DRAWINGS

FIG. 9 is a flow chart of an example process for distributing a video asset to one or more types of user device using the video provisioning system.

DETAILED DESCRIPTION OF PREFERRED EMBODIMENTS

The following detailed description refers to the accompanying drawings. The same reference numbers in different drawings may identify the same or similar elements.

Systems and/or methods, described herein, may enable a synchronization operation to be performed on one or more devices, associated with a video provisioning system (VPS), to ensure that each of the devices, that distribute video assets to different types of user devices, store the same video assets. Ensuring that each of the devices store the same video assets, may allow a set top box to obtain the same video assets as another user device that is a different type of user devices than the set top box. For example, the set top box that obtains video assets, from a first device associated with the VPS, may have access to the same video assets as a different type of user device that obtains video assets, from a second device associated with the VPS, when the first device and the second device are synchronized. The different types of user devices may, for example, include computer devices (e.g., desktop computers, laptop computers, and tablet computers), wireless handset devices (e.g., mobile phones, smart phones, personal digital assistants (PDAs), and tablet computers), and/or set top boxes.

The systems and/or methods may enable a video asset, that is no longer available for distribution to the user devices, to be stored in the VPS when the video asset has been purchased, at a prior time, by at least one of the user devices. The systems and/or methods may that enable a catalog, associated with a user, to include information regarding transactions corresponding to a set top box associated with the user and/or other transactions corresponding to another other user device, associated with the user, that is a different type of user device than the set top box.

Figure 1:
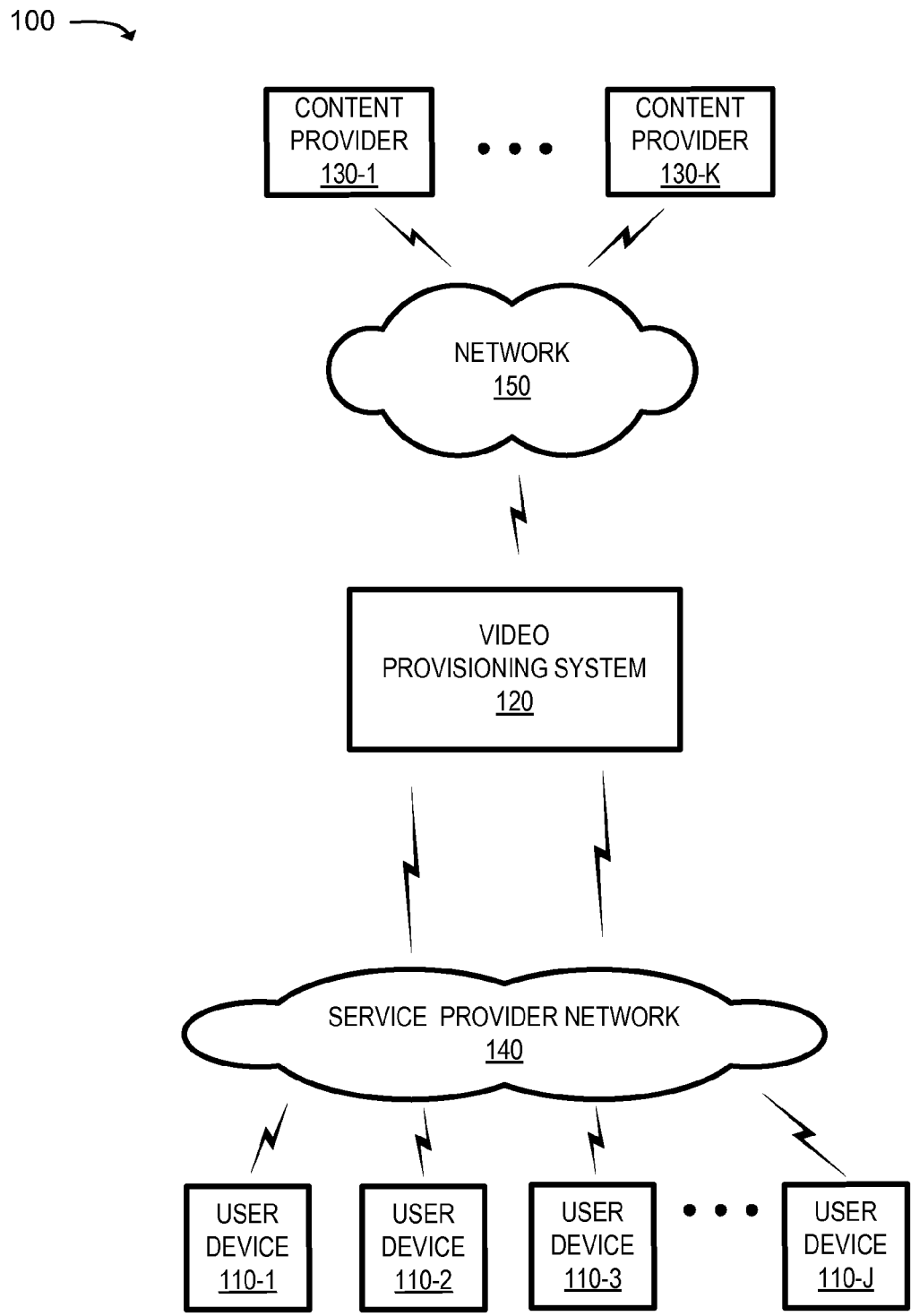
FIG. 1 is a diagram of an example environment in which the systems and/or methods, described herein, may be implemented.

FIG. 1 is a diagram of an example environment in which the systems and/or methods, described herein, may be implemented. As shown in FIG. 1, environment 100 may include a group of user devices 110-1, ..., 110-J (where J≥1) (hereinafter referred to collectively as "user devices 110" and individually as "user device 110"), a video provisioning system (VPS) 120, a group of content providers 130-1, ..., 130-K (where K≥1) (hereinafter referred to collectively as "content providers 130" and individually as "content provider 130"), a service provider network 140, and a network 150. The number of devices, systems, and/or networks, illustrated in FIG. 1, is provided for explanatory purposes only. In practice, there may be additional devices, systems, and/or networks; fewer devices, systems, and/or networks; different devices, systems, and/or networks; or differently arranged devices, systems, and/or networks than illustrated in FIG. 1.

Also, in some implementations, one or more of the devices of environment 100 may perform one or more functions described as being performed by another one or more of the devices of environment 100. Devices, systems, and/or networks of environment 100 may interconnect via wired connections, wireless connections, or a combination of wired and wireless connections.

User device 110 may include a computation or communication device that is capable of communicating with service provider network 140. For example, user device 110 may include a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), a laptop computer, a tablet computer, a set top box, a digital video recorder (DVR), a personal gaming system, a smart phone, or another type of computation or communication device.

User device 110 may communicate with VPS 120 and/or perform certain operations to obtain a video asset from VPS 120. For example, user device 110 may access a portal (e.g., a website, a user interface, an interactive program guide (IPG), an interactive media guide (IMG), etc.) associated with VPS 120, to browse, search, select, and/or obtain a video asset.

VPS 120 may include one or more devices that gather, process, search, store, and/or provide information in a manner similar to that described herein. VPS 120 may be capable of communicating with content providers 130 via network 150 and/or user devices 110 via service provider network 140. VPS 120 may provide a video provisioning service to user devices 110.

VPS 120 may, for example, perform operations associated with video content ingestion, processing, and/or distribution for one or more types of user devices 110, associated with a user, within environment 100. VPS 120 may communicate with one or more content providers 130 to acquire video content. VPS 120 may connect to a collection of various types user devices 110 associated with a user, such as, for example, a set top box, a computer device, a wireless handset device (e.g., a smart phone, a personal digital assistant (PDA), etc.), and/or other types of user devices 110. VPS 120 may connect to the set top box via a television service provider network 140 (e.g., a cable television network, a satellite television network, a fiber optic television network, or some combination thereof). VPS 120 may connect to the computer device via a broad band service provider network 140 (e.g., via the Internet). VPS 120 may connect to the wireless handset device via a wireless service provider network 140. VPS 120 may perform an ingestion operation on the acquired video content. VPS 120 may process and/or publish the ingested video content in a manner that allows the video content to be offered and/or distributed to the different types of user devices 110.

Content provider 130 may include any type or form of content provider. For example, content provider 130 may include free television broadcast providers (e.g., local broadcast providers, such as NBC, CBS, ABC, and/or Fox), for-pay television broadcast providers (e.g., TNT, ESPN, HBO, Cinemax, CNN, etc.), and/or Internet-based content providers (e.g., Youtube, Vimeo, Netflix, Hulu, Veoh, etc.) that stream content from web sites and/or permit content to be downloaded (e.g., via progressive download, etc.). Content provider 130 may include on-demand content providers (e.g., video on demand (VOD), pay per view (PPV), etc.). A media stream, as used herein, may refer to a stream of content that includes video content (e.g., a video stream), audio content (e.g., an audio stream), and/or textual content (e.g., a textual stream).

The term video asset, as used herein, may include VOD content, pay-per-view (PPV) video content, rented video content, free television content (e.g., from free television broadcasters, etc.), paid for television content (e.g., from pay television content providers), on-line video content (e.g., on-line television programs, movies, videos, etc.), advertising, games, music videos, promotional information (e.g., such as previews, trailers, etc.), etc. A video asset may be stored in one or more video files that contain video information that can be played on a user device.

Service provider network 140 may include one or more wired and/or wireless networks via which user devices 110 communicate with and/or receive video content from VPS 120. For example, service provider network 140 may include a cellular network, the Public Land Mobile Network (PLMN), a second generation (2G) network, a third generation (3G) network, a fourth generation (4G) network (e.g., a long term evolution (LTE) network), a fifth generation (5G) network, and/or another network. Additionally, or alternatively, service provider network 140 may include a code division multiple access (CDMA) network, a global system for mobile communications (GSM) network, a general packet radio services (GPRS) network, or a combination of CDMA, GSM, and/or GPRS networks. Additionally, or alternatively, service provider network 140 may include a wide area network (WAN), a metropolitan area network (MAN), an ad hoc network, an intranet, a fiber optic-based network (e.g., a fiber optic service (FiOS) network), a television network, and/or a combination of these or other types of networks.

Network 150 may include one or more wired and/or wireless networks. For example, network 150 may include a cellular network, the PLMN, a 2G network, a 3G network, a 4G network (e.g., an LTE network), a 5G network, and/or another network. Additionally, or alternatively, network 150 may include a WAN, a MAN, a telephone network (e.g., the Public Switched Telephone Network (PSTN)), an ad hoc network, an intranet, the Internet, a fiber optic-based network, and/or a combination of these or other types of networks.

Figure 2:
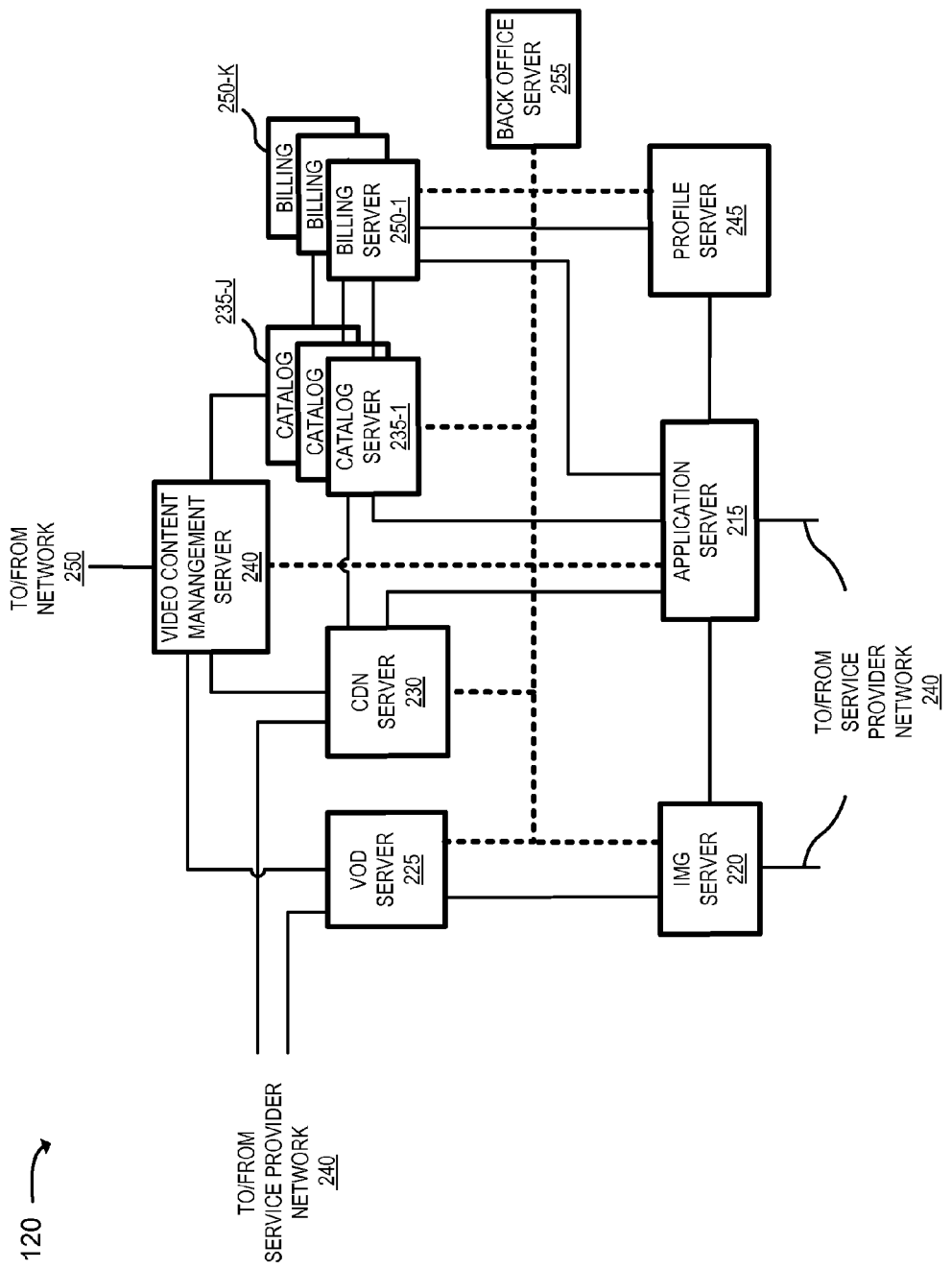
FIG. 2 is a diagram of example devices, associated with the video provisioning system, of FIG. 1.

FIG. 2 is a diagram of example devices associated with VPS 120. VPS 120 may include an application server 215, an interactive media guide (IMG) server 220, a video on-demand (VOD) server 225, a content delivery network (CDN) server 230, a group of catalog servers 235-1, . . . , 235-J (where J≥1) (hereinafter referred to collectively as "catalog servers 235" and individually as a "catalog server 235"), a video content management (VCM) server 240, a profile server 245, a group of billing servers 250-1, . . . 250-K (where K≥1) (hereinafter referred to collectively as "billing servers 250" and individually as a "billing server 250"), and a back office server 255 (hereinafter referred to as "BOS 255"). Although FIG. 2 shows example devices of VPS 120, in other implementations, VPS 120 may include fewer devices, additional devices, different devices, or differently arranged devices than depicted in FIG. 2. Additionally, or alternatively, one or more devices of VPS 120 may perform one or more tasks described as being performed by one or more other devices of VPS 120.

In the description below, VOD server 225 is described as provisioning video services for a type of user device 110 (i.e., a set top box) and CDN server 230 is described as provisioning video services for another type of user device 110 (i.e., a computer device, a wireless handset device, etc.) for explanatory purposes. In another implementation, the video services may be provisioned for the set top box and/or the other types of user devices 110 in a number of ways. For example, VOD server 225 and/or CDN server 230 may be combined into a single device that provisions the video services for each type of user device 110. In another example, the video services may be provisioned, for each type of user device 110, by another device and/or network instead of, or in combination with, VOD server 225 and/or CDN server 230. Additionally, IMG server 220 is described as providing an a store front portal (i.e., via an IMG), that can be accessed by the set top box, and application server 215 is described as providing another store front portal (e.g., via a web page, a user interface, an interactive program guide, etc.), that can be accessed by the other types of user devices 110, for explanatory purposes. In another implementation, the store front portal may be provisioned for the set top box and/or the other types of user devices 110 in a number of ways. For example, IMG server 220 and/or application server 215 may be combined into a single device that provisions the store front portal for each type of user device 110. In another example, the store front portal may be provisioned, for each type of user device 110, by another device and/or network instead of, or in combination with, IMG server 220 and/or application server 215. Thus, the examples below are provided for explanatory purposes only.

Application server 215 may include one or more server devices, or other types of computation or communication devices, that gather, process, search, store, and/or provide information in a manner similar to that described herein. Application server 215 may receive metadata that has been published by catalog server 235.

Metadata may enable the video assets to be identified, managed, offered, and/or distributed to a user device. The metadata may, for example, include an identifier associated with a video asset (e.g., a number, a name, a title, etc.); a genre of the video asset (e.g., horror, comedy, adult, etc.); a category of the video asset (e.g., VOD asset, a PPV asset, an on-line asset, etc.); a text description, a key word index, and/or summary of the video asset; an image (e.g., cover art) associated with the video asset, and/or information associated with artists associated with the video asset (e.g., names of actors, directors, producers, etc.). The metadata may also, or alternatively, include information associated with a type of video asset (e.g., a movie, music video, a game, etc.); a rating associated with the video asset (e.g., general audience (G), parental guidance (PG), PG-13, restricted (R), mature audience (MA), etc.); user reviews associated with the video asset; a price associated with the video asset (e.g., a sale price, a rental price per day, a pay-per-view price, etc.); and/or an availability period associated with the video asset (e.g., release dates, restriction periods, blackout periods, etc.). The metadata may also, or alternatively, include information associated with a storage location (e.g., a uniform resource locator (URL)) corresponding to the video asset; a format associated with the video asset (e.g., a resolution level, compression/decompression (CODEC) information, a screen size, a frame size, a frame refresh rate, a bit rate, etc.); and/or types of user devices supported by each format, etc.

The metadata may be associated with video assets that are to be made available and/or offered (e.g., for sale, rent, subscription, etc.) to user devices 110. Application server 215 may host a portal (e.g., a VPS store front), such as a private website (e.g., for subscribing user devices 110), a public website (e.g., for non-subscribing user devices 110), a user interface (UI) (e.g., that is accessible by wireless handset user devices 110, etc.), an interactive program guide (e.g., an IMG for set top box-type user devices 110) and/or other types of user interfaces. The portal may enable single sign-on (SSO) portal access, to a user of one or more user devices 110, based on the same login credentials (e.g., username, password, personal identification number (PIN), etc.). Application server 215 may publish all or a portion of the metadata to the portal that permits any of user devices 110 to browse, perform searches, process payment, etc. for video assets based on the metadata that is published to the portal.

Application server 215 may store information associated with a transaction history that corresponds to a type of user device 110 (e.g., a computer user device 110, a wireless handheld user device 110, a gaming user device 110, etc.) that is different than a set top box user device 110. The transaction history may include information regarding prior transactions (e.g., purchases, rentals, subscriptions, etc.), associated with one or more video assets, by user device 110. The transaction history may also identify a period of time during which a rental period or subscription period, for a video asset, is valid. Application server 215 may, in another example, transmit information, associated with the transaction history, to profile server 245, to be stored in a user profile associated with a user of user device 110. IMG server 220 may include one or more server devices, or other types of computation or communication devices, that gather, process, search, store, and/or provide information in a manner similar to that described herein. IMG server 220 may, for example, process metadata, that has been published by catalog server 235 and/or VOD server 225, in a manner similar to that described above (e.g., with respect to application server 215). The metadata may be associated with video content that may be obtained by a particular type of user device 110, such as a set top box user device 110.

IMG server 220 may publish all or a portion of the metadata to an IMG UI that the set top box user device 110, associated with the user, may render for display on a video display device. IMG server 220 may permit the set top box user device 110 to access information associated with video assets, stored by VOD server 225, and access the actual video assets. IMG server 220 may, in another example implementation, communicate with application server 215, which may permit the set top box user device 110 to access the metadata associated video assets that are stored in CDN server 230.

IMG server 220 may store information associated with a transaction history that corresponds to a set top box user device 110. The transaction history may include information regarding prior transactions (e.g., purchases, rentals, subscriptions, etc.), associated with one or more video assets, by set top box user device 110. The transaction history may also identify a period of time during which a rental period or subscription period, for a video asset, is valid. Application server 215 may, in another example, transmit information, associated with the transaction history, to profile server 245, to be stored in a user profile associated with a user of user device 110.

VOD server 225 may include one or more server devices, or other types of computation or communication devices, that gather, process, search, store, and/or provide information in a manner similar to that described herein. VOD server 225 may, for example, perform operations to receive, store, process, and/or distribute video content in a format that is supported by set top box user devices 110.

VOD server 225 may receive published video assets and/or metadata from VCM server 240. VOD server 225 may store the published video assets in a memory associated with VOD server 225. VOD server 225 may publish a portion of the metadata, associated with video assets (e.g., that are available for release and/or not subject to a blackout, etc.), to IMG server 220. In another example implementation, VOD server 225 may communicate with content provider 130 to receive video content directly from content provider 130 (e.g., not via VCM server 240).

CDN server 230 may include one or more server devices, or other types of computation or communication devices, that gather, process, search, store, and/or provide information in a manner similar to that described herein. CDN server 230 may, for example, perform operations to receive, store, process, and/or distribute video content in a format that is supported by one or more types of user devices 110 (e.g., a computer device, a wireless mobile device, a gaming device, etc.) other than, or in addition to, a set top box user device 110. CDN server 230 may actually represent a content delivery network that includes multiple routing and/or storage devices.

CDN server 230 may receive published video assets in multiple video formats from VCM server 240. CDN server 230 may store the published video assets in a memory associated with CDN server 230. CDN server 230 may identify a respective storage location and/or URL for each format of each video asset that are stored within the memory and may send information associated with the storage locations and/or the URLs to catalog server 235. CDN server 230 may provide video assets to wireless handset user devices 110 via a wireless service provider network 140. CDN server 230 may provide the video assets to a computer user device 110 via a broadband service provider network 140 (e.g., the Internet). In another example implementation, CDN server 230 may provide the video assets to a set top box user device 110 via a television service provider network 140 and/or via VOD server 225.

Catalog server 235 may include one or more server devices, or other types of computation or communication devices, that gather, process, search, store, and/or provide information in a manner similar to that described herein. Catalog server 235 may, for example, receive, from VCM server 240, published metadata associated with video assets that have been published to VOD server 225 and/or CDN server 230. Catalog server 235 may identify, from the metadata, information associated with the availability of the video assets based on dates on which the video assets are released, blacked out, etc. Catalog server 235 may process and/or package the metadata in order to offer, to user devices 110, the video assets to which the metadata corresponds. The processed metadata, associated with the video assets, may include identifiers (e.g., video asset numbers, titles, etc.), prices (e.g., sale prices, rental prices, subscription prices, etc.), descriptions (e.g., a synopsis, a summary, etc. of the video assets), ratings, reviews, genres, casting information (e.g., actors, directors, producers, etc.), etc. Catalog server 235 may, for example, publish the metadata to the store front portal associated with VPS application 215. Catalog server 235 may not publish metadata associated with video assets that are identified as not yet being available.

One catalog server 235, such as catalog server 235-1, may store metadata associated with video assets that are accessible by wireless handset user devices 110 (e.g., via a wireless service provider network 140). Another catalog server 235, such as catalog server 235-2, may store metadata associated with video assets that are accessible by computer user devices 110 (e.g., via a broadband service provider network 140). Yet another catalog server 235, such as catalog server 235-J, may store metadata associated with video assets that are accessible by set top box user devices 110 (e.g., via a television service provider 140).

VCM server 240 may include one or more server devices, or other types of computation or communication devices, that gather, process, search, store, and/or provide information in a manner similar to that described herein. VCM server 240 may, for example, communicate with content providers 130 to ingest video assets to be processed by VPS 120. VCM server 240 may process the video assets to generate copies of the video assets in one or more formats that are supported (e.g., that can be received, processed, and/or played) by the different types of user devices 210. VCM server 240 may publish the one or more formats, associated with the processed video assets, to VOD server 225 and/or CDN server 230.

VCM server 240 may also ingest, process, and/or publish metadata associated with the video assets. VCM server 240 may process the metadata to ensure that the metadata is supported by the different types of user devices 210. VCM server 240 may publish the processed metadata to catalog server 235.

Profile server 245 may include one or more server devices, or other types of computation or communication devices, that gather, process, search, store, and/or provide information in a manner similar to that described herein. Profile server 245 may, for example, store information associated with a profile that includes information regarding the user and/or each user device 110 that the user has registered with VPS 120. For example, information associated with the profile may further include information associated with the user (e.g., a username, password, PIN, etc.), information associated with each user device 110, such as a respective identifier (e.g., a mobile directory number (MDN), an Internet protocol (IP) address, a media access control (MAC) address, a compression/decompression (CODEC) identifier, etc.), and/or information associated with a type of user device 110, such as a computer device (e.g., a lap top computer, a tablet computer, etc.), a wireless mobile device (e.g., a Droid®, a Blackberry®, an iPhone®, etc.), a set top box, a gaming device, etc.

The information associated with the profile may also include a respective transaction history (e.g., prior purchases, prior URLs accessed, prior downloads, etc.) associated with each user device 110; information associated with services for which user device 110 has subscribed; information associated with a location (e.g., an address, a zip code, a city, etc.) of the user and/or user device 110; information associated user account limits, restrictions, etc.; information associated with a language spoken by the user; etc. Profile server 245 may communicate with application server 215 to obtain a first transaction history, associated with user device 110, that are different types of user devices 110 than a set top box user device 110, such as a computer user device 110, a wireless handheld user device 110, a gaming user device 110, etc. Profile server 245 may communicate with IMG server 220 to obtain a second transaction history, associated with a set top box user device 110. Profile server 245 may store information obtained from the first transaction history and/or the second transaction history in a user profile associated with a user of the set top box user device 110 and/or user device 110.

The information associated with the profile may include a bookmark that identifies a location at which user device 110 stopped a video asset. The bookmark may permit another user device 110, associated with the user, to resume playing the video asset (e.g., that has been downloaded on the other user device 110) at the location at which the video asset was stopped by user device 110.

Billing server 250 may include one or more server devices, or other types of computation or communication devices, that gather, process, search, store, and/or provide information in a manner similar to that described herein. Billing server 250 may, for example, perform billing operations associated with accounts that correspond to each user device 110 associated with a user. For example, billing server 250 may receive an indication that user device 110 (e.g., a computer device), associated with the user, downloaded a video asset (e.g., via a broadband service associated with service provider network 240) as a result of a transaction via the store front portal. Billing server 250 may generate billing information that identifies the video asset, the type of transaction (e.g., a purchase, rental, subscription, etc.), a price associated with the transaction, a time at which the transaction occurred, etc. Billing server 250 may associate the billing information with an account that corresponds to the user and/or user device 110. Billing server 250 may generate other billing information regarding another transaction with another user device 110 (e.g., a set top box) with which the user is associated. Billing server 250 may associate the other billing information with another account that corresponds to the user and/or the other user device 110. In yet another example, billing server 250 may process payment information (e.g., based on credit card information, debit card information, etc.) associated with a transaction with a further user device 110 to purchase, rent, subscribe to, etc. another video asset.

BOS 255 may include one or more server devices, or other types of computation or communication devices, that gather, process, search, store, and/or provide information in a manner similar to that described herein. BOS 255 may, for example, communicate with VOD server 225 and/or CDN server 230 to perform a synchronization operation. The synchronization operation may ensure that video assets that are stored in VOD server 225 are also stored in CDN server 230 and/or that the video assets that are stored in CDN server 230 are also stored in VOD server 225. The synchronization operation may ensure that the video assets are accessible to the different types of user devices 110 (e.g., set top boxes, computer devices, wireless handheld devices, gaming devices, etc.). If BOS 255 determines that VOD server 225 and/or CDN server 230 is missing a video asset, BOS 255 may communicate with VCM server 240 to obtain the missing video asset in a format identified by BOS 255. In another example, BOS 255 may, in a manner similar to the synchronization operation with respect to VOD server 225 and CDN server 230, perform a synchronization operation on catalog server 235 to ensure that each catalog server 235 stores the same metadata that corresponds to the video assets.

BOS 255 may instruct VOD server 225 and/or CDN server 230 to archive (e.g., permanently store) a video asset that is determined to no longer be available for distribution to user devices 110 (e.g. based on terms and/or conditions imposed by content provider 150). BOS 255 may instruct VOD server 225 and/or CDN server 230 to archive the video assets based on a determination that the video asset has been distributed to at least one user device 110 as a result of a prior purchase. BOS 255 may instruct VOD server 225 and/or CDN server 230 to delete the video asset based on a determination that the video asset has not been distributed to at least one user device 110, as a result of a prior purchase. In another example implementation, BOS 255 may instruct VOD server 225 and/or CDN server 230 to archive the video assets based on a determination that the video asset has been distributed to at least one user device 110 as a result of a prior rental and/or subscription. BOS 255 may, in this implementation, instruct VOD server 225 and/or CDN server 230 to delete the video asset based on a determination that the video asset has not been distributed to at least one user device 110, as a result of a prior rental, subscription, or purchase.

BOS 255 may instruct catalog server 235 to archive metadata, associated with the video asset, based on the determination that the video asset has been distributed to at least one user device 110, as a result of a prior purchase. When archiving the metadata, BOS 255 may instruct catalog server 235 that the metadata is not to be accessible to user devices 110 unless a user device 110 is associated with the prior purchase. BOS 255 may instruct catalog server 235 to delete the metadata based on the determination that the video asset has not been distributed to at least one user device 110, as a result of a prior purchase.

BOS 255 may allow user device 110 to obtain a video asset, that is being received via a video stream from content provider 130, from VOD server 225 (e.g., if user device 110 is a set top box) and/or CDN server 230 (e.g., if user device 110 is a type of user device 110 that is different than a set top box). Allowing user device 110 to obtain the video asset from VOD server 225 and/or CDN server 230 may enable user device 110 to control the video asset (e.g., fast forward, rewind, pause, etc.) and/or store the video asset.

BOS 255 may instruct profile server 245 to synchronize information associated with one or more transaction histories regarding user devices 110 associated with a user. BOS 255 may, for example, instruct profile server 245 to store, in a user profile associated with the user, information regarding a first transaction history, regarding a user device 110 associated with the user, that is different a different type of user device 110 than a set top box user device 110. BOS 255 may, in another example, instruct profile server 245 to store, in the user profile, information regarding a second transaction history regarding a set top box user device 110 associated with the user.

BOS 255 may enable user device 110 to perform a unified search for information associated with a video asset. BOS 255 may perform the unified search by searching for the information associated with the video asset from IMG server 220 and/or one or more catalog servers 230, such as, for example, catalog server 230-1 associated with computer user devices 110, catalog server 230-2 associated with wireless handheld user devices 110, etc. BOS 255 may obtain information associated with the video asset IMG server 220 and/or the one or more catalog servers 235 and may send the information associated with the video asset to user device 110. Performing the unified search may ensure that a search, performed by each type of user device 110, produces a same result regardless of the type of user device 110 that performed the search.

BOS 255 may enable a user, of user device 110, to specify respective parental controls for each type of user device 110, such as a set top box, a computer device, a wireless handheld device, a gaming device, etc. BOS 255 may, for example, allow a user, of a computer device, to specify parental controls for the computer device. BOS 225 may allow the user to specify other parental controls for a wireless handheld device. BOS 225 may allow the user to specify further parental controls for a set top box. BOS 255 may allow the user to establish a same set of parental controls (e.g., global parental controls) that apply to the set top box, the computer device, the wireless handheld device, the gaming device, etc. BOS 255 may permit the user (e.g., as a master user) to override parental controls that are set for any of the different types of user devices 110. BOS 255 may permit the user to specify that all or a portion of the global parental controls override parental controls that are set for any of the different types of user devices 110.

Figure 3:
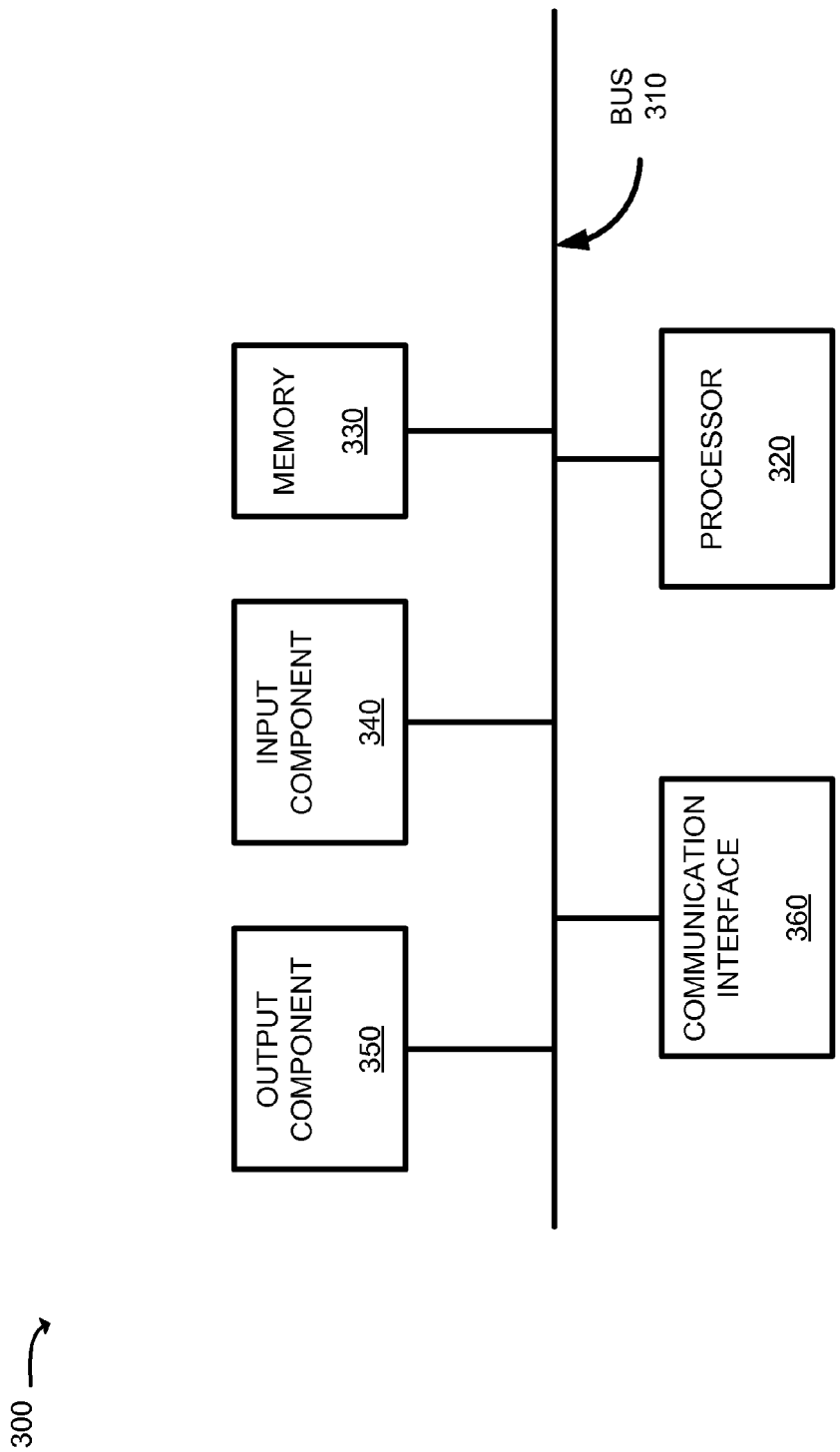
FIG. 3 is a diagram of example components that correspond to one or more of the devices of FIGS. 2 and/or 3.

FIG. 3 is a diagram of example components of a device 300 that may correspond to user device 110, content provider 130, application server 215, IMG server 220, VOD server 225, CDN server 230, catalog server 235, VCM server 240, profile server 245, billing server 250, and/or BOS 255. Alternatively, each of user device 110, content provider 130, application server 215, IMG server 220, VOD server 225, CDN server 230, catalog server 235, VCM server 240, profile server 245, billing server 250, and/or BOS 255 may include one or more devices 300. Device 300 may include a bus 310, a processor 320, a memory 330, an input component 340, an output component 350, and a communication interface 360. Although FIG. 3 shows example components of device 300, in other implementations, device 300 may contain fewer components, additional components, different components, or differently arranged components than depicted in FIG. 3. For example, device 300 may include one or more switch fabrics instead of, or in addition to, bus 310. Additionally, or alternatively, one or more components of device 300 may perform one or more tasks described as being performed by one or more other components of device 300.

Bus 310 may include a path that permits communication among the components of device 300. Processor 320 may include a processor, microprocessor, or processing logic that may interpret and execute instructions. Memory 330 may include any type of dynamic storage device that may store information and instructions, for execution by processor 320, and/or any type of non-volatile storage device that may store information for use by processor 320.

Input component 340 may include a mechanism that permits a user to input information to device 300, such as a keyboard, a keypad, a button, a switch, etc. Output component 350 may include a mechanism that outputs information to the user, such as a display, a speaker, one or more light emitting diodes (LEDs), etc. Communication interface 360 may include any transceiver-like mechanism that enables device 300 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. For example, communication interface 360 may include mechanisms for communicating with another device or system via a network, such as service provider network 140 and/or network 150. In one alternative implementation, communication interface 360 may be a logical component that includes input and output ports, input and output systems, and/or other input and output components that facilitate the transmission of data to other devices.

As will be described in detail below, device 300 may perform certain operations relating to back office support for a video provisioning system. Device 300 may perform these operations in response to processor 320 executing software instructions contained in a computer-readable medium, such as memory 330. A computer-readable medium may be defined as a non-transitory memory device. A memory device may include space within a single physical memory device or spread across multiple physical memory devices. The software instructions may be read into memory 330 from another computer-readable medium or from another device. The software instructions contained in memory 330 may cause processor 320 to perform processes described herein. Alternatively, hardwired circuitry may be used in place of or in combination with software instructions to implement processes described herein. Thus, implementations described herein are not limited to any specific combination of hardware circuitry and software.

Figure 4:
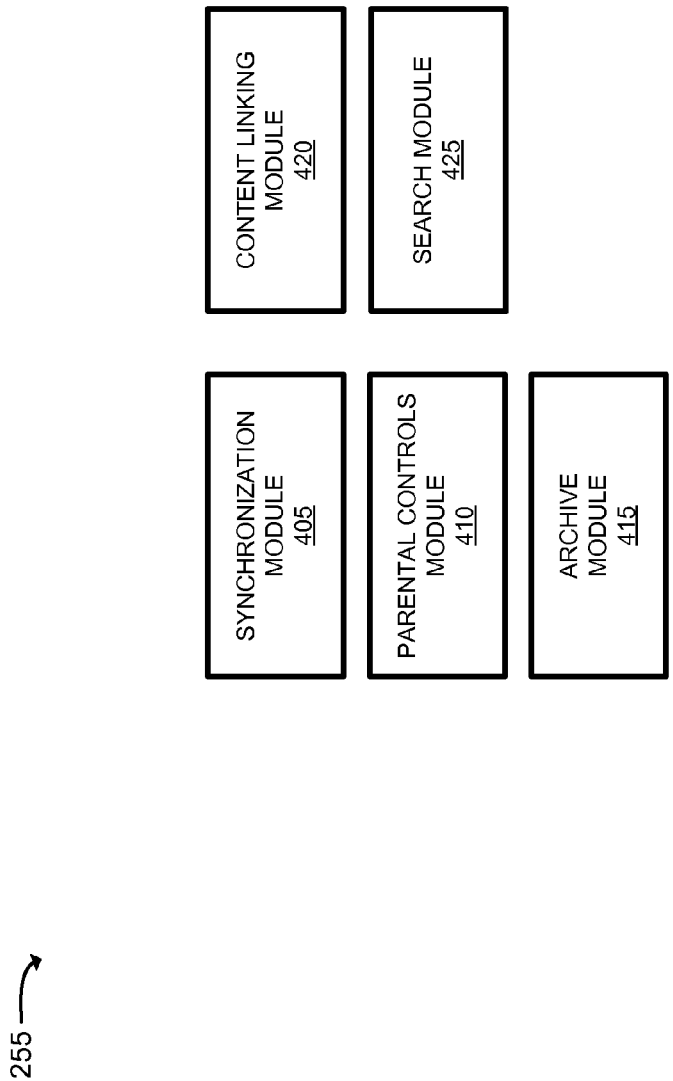
FIG. 4 is a diagram of example functional components that correspond to a back office server of FIG. 2.

FIG. 4 is a diagram of example functional components 400 of BOS 255. As shown in FIG. 4, BOS 255 may include a collection of functional components, such as a synchronization module 405, a parental controls module 410, an archive module 415, a content linking module 420, and a search module 425. Although FIG. 4 shows example functional components of BOS 255, in other implementations, BOS 255 may contain fewer functional components, additional functional components, different functional components, or differently arranged functional components than depicted in FIG. 4. For example, one or more functional components may be combined into a single functional component. Additionally, or alternatively, one or more functional components of BOS 255 may perform one or more tasks described as being performed by one or more other functional components of BOS 255.

In the description below, each functional component, of BOS 255, is described as being hosted by BOS 255 for explanatory purposes. In another implementation, each of the functional components may be hosted by any of the devices associated with VPS 120 and/or one or more other devices separate from, or in combination with, the devices associated with VPS 120.

Synchronization module 405 may include logic, implemented using hardware or a combination of hardware and software, that allows devices, associated with VPS 120, to be synchronized in a manner similar to that described above in FIG. 2. Synchronization module 405 may include a synchronization application programming interface (API) that enables synchronization module to communicate with IMG server 220, VOD server 225, CDN server 230, catalog server 235, and/or VCM server 240. For example, synchronization module 405 may ensure that the same video assets are stored in VOD server 225 and CDN server 230 in a manner similar to that described above in FIG. 2. Synchronization module 405 may obtain a video asset, from VCM server 240, that is determined to be missing from VOD server 225 and/or CDN server 230. Synchronization module 405 may ensure that metadata, stored in IMG server 220 and/or catalog server 235, corresponds to the video assets stored in CDN server 230. Synchronization module 405 may cause information associated with a transaction history regarding a set top box user device 110, associated with a user, to be included in a user profile associated with the user. Synchronization module 405 may cause information associated with another transaction history regarding a another type of user device 110, associated with a user, to be included in the user profile.

Parental controls module 410 may include logic, implemented as hardware or a combination of hardware and software, that enables respective parental controls to be established and/or implemented in a manner similar to that described above in FIG. 2. Parental controls module 410 may include a parental controls API that enables parental control module 410 to communicate with application server 215, IMG server 220, catalog server 235, and/or profile server 245 when establishing and/or implementing parental controls. Parental controls module 410 may enable respective parental controls to be established for different types of user devices 110 associated with a user. Parental controls module 410 may allow global parental controls to be established and/or implemented for all or a portion of the different types of user devices 110 associated with the user.

Archive module 415 may include logic, implemented as hardware or a combination of hardware and software, that ensures that video assets and/or metadata are archived in a manner similar to that described above in FIG. 2. Archive module 415 may include an archive API that enables archive module 415 to communicate with IMG server 220, VOD server 225, and/or CDN server 230 and/or catalog server 235 when performing an archive operation. Archive module 415 may, for example, cause a video asset, that is no longer available, to be archived, by VOD server 225 and/or CDN server 230, when the video asset has been purchased at a prior time. Archive module 415 may cause a video asset, that is not available, to be discarded, by VOD server 225 and/or CDN server 230, when the video asset has not been purchased at the prior time.

Content linking module 420 may include logic, implemented as hardware or a combination of hardware and software, that enables a content linking operation to be performed in a manner similar to that described above in FIG. 2. Content linking module 420 may include a linking API that enables content linking module 420 to communicate with IMG server 220, VOD server 225, application server 215, and/or CDN server 230 when performing the content linking operation. Content linking module 420 may, for example, detect when user device 110 is receiving a video asset, as a live video stream, from content provider 130 and may determine whether the video asset is stored by VOD server 225 and/or CDN server 230. Content linking module 420 may instruct VOD server 225 and/or CDN server 230 to transmit a copy of the video asset to user device 110.

Search module 425 may include logic, implemented as hardware or a combination of hardware and software, that enables a uniform search operation to be performed in a manner similar to that described above in FIG. 2. Search module 425 may include a search API that enables search module 425 to communicate with IMG server 220 and/or one or more catalog servers 235 to obtain information associated with a video asset in response to a search query received from user device 110.

Figure 5:
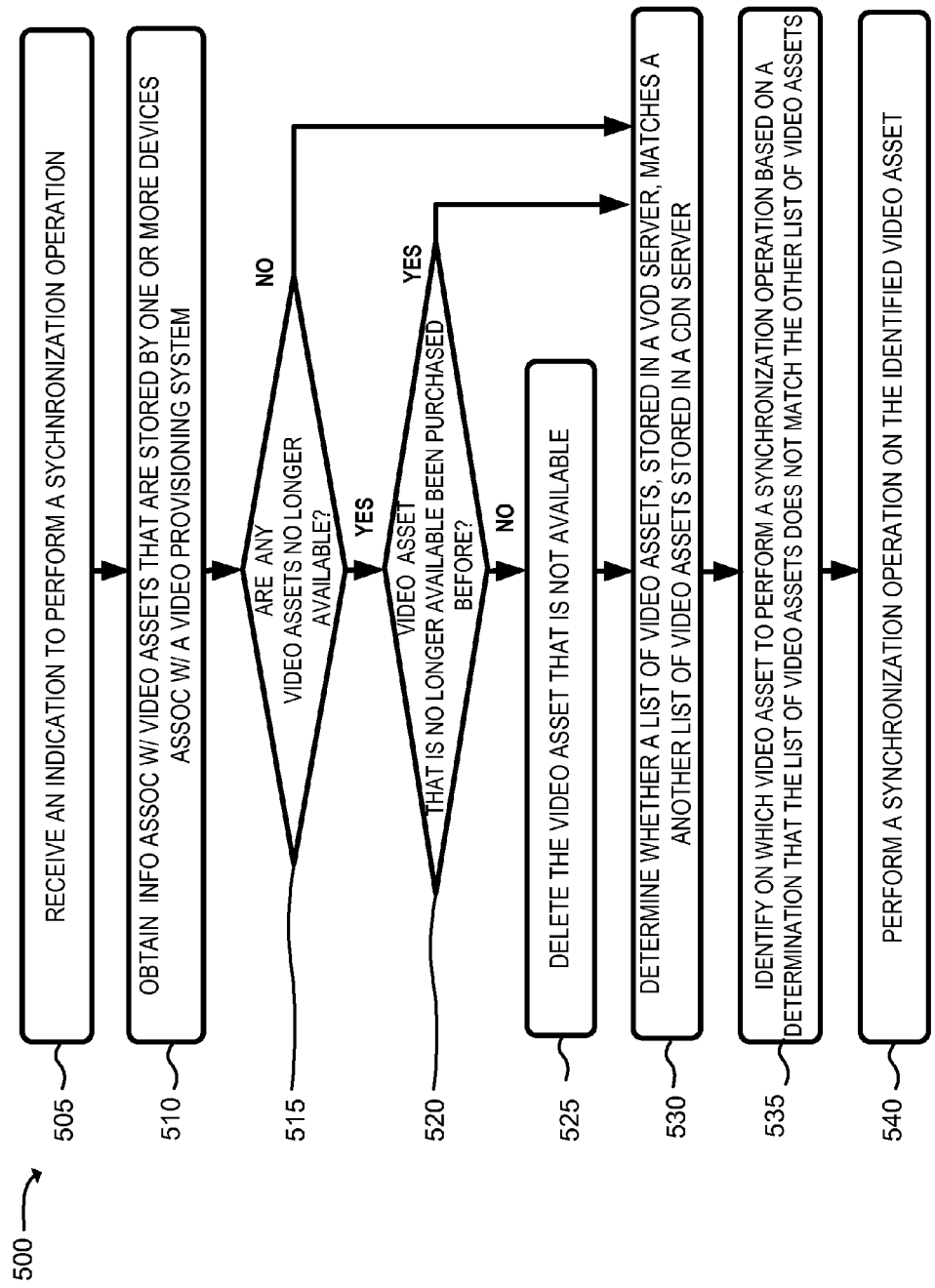
FIG. 5 is a flow chart of an example process for synchronizing video assets that are stored in one or more devices associated with a video provisioning system.

FIG. 5 is a flow chart of an example process 500 for synchronizing video assets that are stored in one or more devices associated with a VPS 120. In one example implementation, process 500 may be performed by BOS 255. In another example implementation, some or all of process 500 may be performed by a device, or collection of devices separate from, or in combination with BOS 255.

As shown in FIG. 5, process 500 may include receiving an indication to perform a synchronization operation (block 505) and obtaining information associated with video assets that are stored in one or more devices associated with a video provisioning system (block 510). For example, BOS 255 may receive an indication to perform a synchronization operation based on a predetermined time interval (e.g., every 12 hours, every 24 hours, etc.), time of day (e.g., at midnight, at 2:00 am, etc.), and/or upon the occurrence of some event (e.g., when triggered by an operator associated with VPS 120, etc.). BOS 255 may, in response to the indication, communicate with VOD server 225 and/or CDN server 230 to retrieve information associated with video assets that are stored by VOD server 225 and/or CDN server 230. The information associated with the video assets may include, for example, a list of video assets (e.g., a list of identifiers, titles, etc.) and/or a list of availability periods that corresponds to the list of video assets that are stored by VOD server 225. The information associated with the video assets may also include another list of video assets and/or another list of availability periods that corresponds to the other list of video assets that are stored by CDN server 230.

As also shown in FIG. 5, if any of the video assets are no longer available (block 515 YES) and if a video asset, that is no longer available, has not been purchased before (block 520—NO), then process 500 includes deleting the video asset that is no longer available. For example, BOS 255 may determine whether a current time does not fall within any of the availability periods associated with the list of availability periods or the other list of availability periods. BOS 255 may identify a video asset that corresponds to an availability period that the current time does not fall within and BOS 255 send an instruction for the video asset to be discarded (e.g., erased, deleted, purged, etc.) from VOD server 225 and/or CDN server 230. BOS 255 may send an instruction to IMG 220 and/or catalog server 235 instructing that metadata, associated with the video asset, is to be discarded.

As further shown in FIG. 5, if none of the video assets are no longer available (block 515—NO), or if any of the video assets are no longer available (block 515—YES) and if a video asset, that is no longer available, has been purchased before (block 520—YES), then process 500 may include determining whether a list of video assets, that are stored in a VOD server, matches another list of video assets that are stored in a CDN server (block 530). Alternatively, as shown in FIG. 5, after deleting the video asset that is not available (block 525), process 500 may include determining whether the list of video assets that are stored in the VOD server, matches the other list of video assets that are stored in the CDN server (block 530). For example, BOS 255 may compare the list of video assets to the other list of video assets to determine whether the list of video assets matches the other list of video assets. BOS 255 may, for example, determine that all of the video assets identified by the list of video assets match all of the video assets identified by the other list of video assets. Based on the determination that the list of video assets matches the other list of video assets, BOS 255 may not perform the synchronization operation. In another example, BOS 255 may determine that all of the video assets identified in the list of video assets do not match all of the video assets identified by the other list of video assets. Based on the determination that all of the video assets identified in the list of video assets do not match all of the video assets identified by the other list of video assets, BOS 255 may perform a synchronization operation.

As yet further shown in FIG. 5, process 500 may include identifying on which video asset to perform a synchronization operation based on a determination that the list of identifiers does not match the other list of identifiers (block 535) and performing a synchronization operation one the identified video asset (block 540). For example, BOS 255 may identify a video asset that is not identified in both the list of video assets and the other list of video assets. BOS 255 may determine that the identified video asset is identified in the list of video assets that are stored in VOD server 225 but is not identified in the other list of assets that are stored in CDN server 230. Based on the determination that the identified video asset is identified in the list of video assets but is not identified in the other list of assets, BOS 255 may instruct VCM server 240 to store a copy of the video asset in CDN server 230. BOS 225 may send another instruction, to VCM server 240 to store metadata, associated with the identified video asset, in catalog server 235.

In another example, BOS 255 may determine that the identified video asset is identified in the other list of video assets that are stored in CDN server 230 but is not identified in the list of assets that are stored in VOD server 225. Based on the determination that the identified video asset is identified in the other list of video assets but is not identified in the list of assets, BOS 255 may instruct VCM server 240 to store a copy of the identified video asset in VOD server 225. BOS 225 may send another instruction, to VCM server 240 to store metadata, associated with the identified video asset, in IMG server 220.

Figure 6:
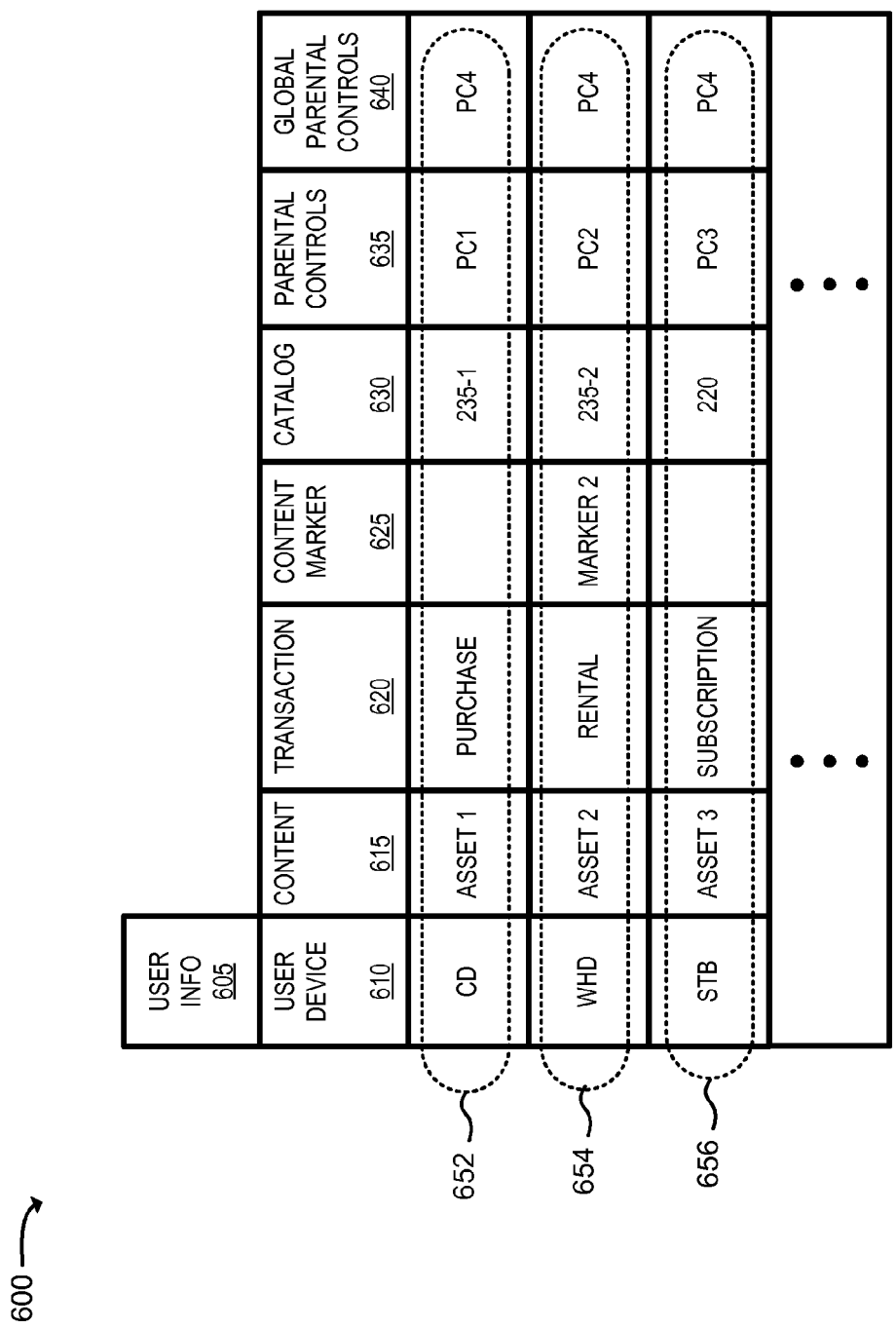
FIG. 6 is a diagram of an example data structure that stores information associated with a user profile of a user associated with a user device.

FIG. 6 is a diagram of a data structure 600 that stores information associated with a profile that corresponds to a user, of user device 110. Data structure 600 may be stored in profile server 245 and/or another memory associated with VCM server 240. Data structure 600 may include a collection of fields, such as, a user information (info) field 605, a user device field 610, a content field 615, a transaction field 620, a content marker field 625, a catalog field 630, a parental controls field 635, and a global parental controls field 640. Data structure 600 may include a number of fields for explanatory purposes. In practice, data structure 600 may include additional fields, fewer fields, different fields, or differently arranged fields than are described with respect to data structure 600.

User info field 605 may store information associated with a user, of a particular user device 110, such as, a username, a password, a personal identification number, etc. Additionally, or alternatively, user device field 610 may store information, associated with the particular user device 110, such as a device identifier (e.g., an MDN, an IMSI, and MSISDN, a CODEC identifier, etc.), an address associated with user device 110 (e.g., a MAC address, an IP address), etc. Content field 615 may store information associated with a video asset, such as a content identifier, a title, etc., that is obtained and/or played by the particular user device 110. Transaction field 620 may store information associated with a manner in which the video asset, identified in content field 615, was obtained (e.g., by purchasing, renting, subscribing, etc.) by the particular user device 110.

Content marker field 625 may store information regarding a point, associated with the video asset identified in content field 615, that the particular user device 110 stopped playing the video asset. Catalog field 630 may store information associated with a catalog (e.g., catalog server 235, IMG server 220, etc.) that stores metadata, associated with available video assets, that are stored in VOD server 225 and/or CDN server 230. In another example implementation, Catalog field 630 may store information associated with a transaction history (e.g., stored in application server 215, IMG server 220, profile server 245, etc.), regarding one or more video assets, that the particular user device 110 has obtained as a result of a transaction (e.g., a transaction to purchase, rent, subscribe to, etc.).

Parental controls field 635 may store information associated with parental controls, associated with the particular user device 110, that were specified by the user of the particular user device 110. The information associated with the parental controls may identify a content genre (e.g., horror, adult, etc.), a rating (e.g., restricted (R), mature audiences (MA), etc.), etc. that are not to be accessed, obtained, and/or played by the particular user device 110. Global parental controls field 640 may store information associated with parental controls that correspond to one or more different types of user devices 110 (e.g., a set top box, a computer device, a wireless handheld device, a gaming device, etc.) associated with the user of the particular user device 110.

BOS 255 may receive an indication that a computer user device 110 has purchased a video asset and may instruct profile server 245 to store, in data structure 600, the information associated with the computer user device 110 (e.g., CD), the type of transaction (e.g., purchase), and/or information associated with the video asset (e.g., asset 1) (e.g., as shown by ellipse 652). BOS 255 may instruct profile server 245 to store information that identifies a particular catalog server 235 (e.g., 235-1) that stores metadata associated with the purchased video asset and/or other video assets that computer user device 110 has access to (e.g., as shown by ellipse 652). Profile server 245 may store information associated with parental controls (e.g., PC1) that corresponds to the computer user device 110 and/or information associated with global parental controls (e.g., PC4) that correspond to the computer user device 110 and/or other types of user devices 110 associated with the user (e.g., as shown in ellipse 652).

In another example, profile server 245 may be instructed to store information associated with other types of user devices 110, such as a wireless handheld user device 110 (e.g., WHD) and/or a set top box user device 110 (e.g., STB), associated with the user, that have obtained video assets (e.g., asset 1 and/or asset 2, respectively) (e.g., as shown by ellipse 654 and 656, respectively). Profile server 245 may also be instructed to store information associated with a type of transaction (e.g., rental and/or subscription), and/or information that identifies a catalog server 235 (e.g., 235-2) and/or IMG server 220 (e.g., 220), respectively, that correspond to wireless handheld user device 110 and/or set top box user device 110, respectively (e.g., as shown by ellipses 654 and 656). Profile server 245 may store information associated with parental controls (e.g., PC2 and PC3) that correspond to the wireless handheld user device 110 and/or the set top box user device 110, respectively (e.g., as shown by ellipses 654 and 656, respectively). Profile server 245 may store information associated with the global parental controls that correspond to the wireless handheld user device 110 and/or set top box user device 110.

Figure 7:
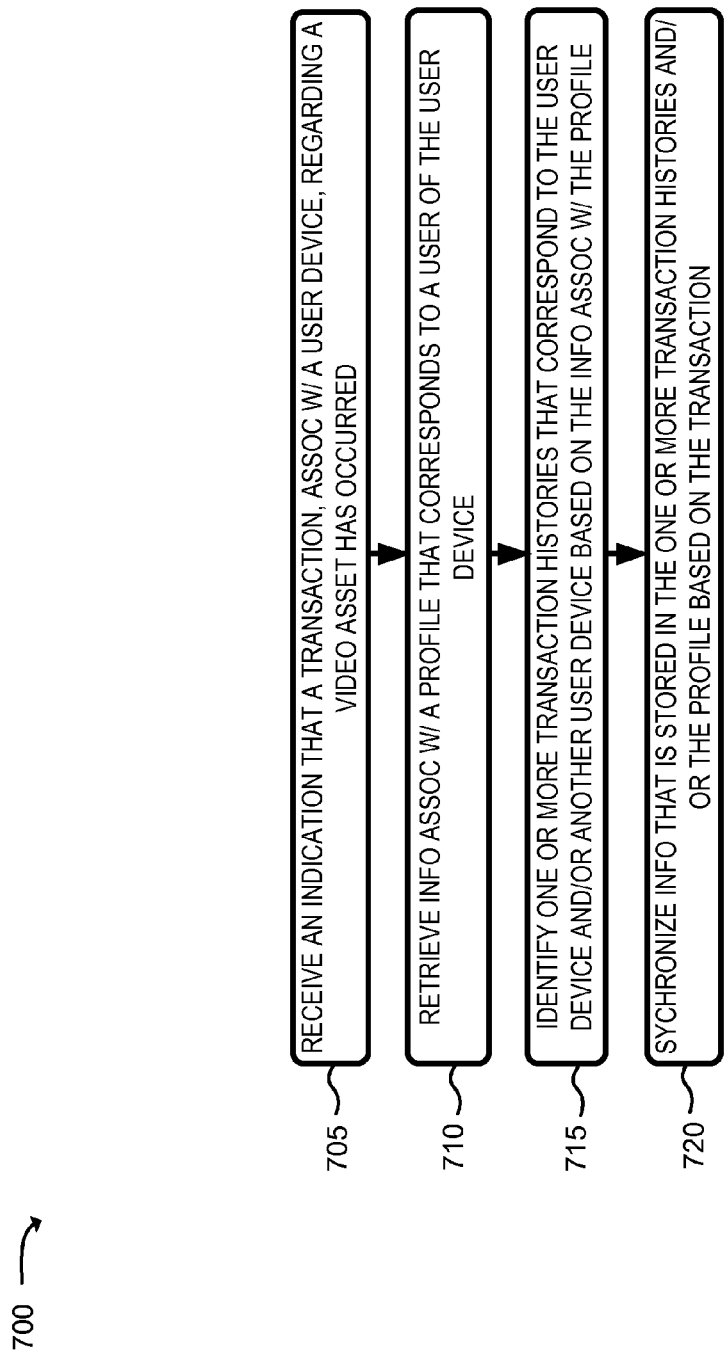
FIG. 7 is a flow chart of an example process for synchronizing transactions between one or more user devices, associated with a user.

FIG. 7 is a flow chart of an example process 700 for synchronizing transactions between one or more user devices 110 that are associated with a user. In an example implementation, process 700 may be performed by BOS 255. In another example implementation, some or all of process 700 may be performed by a device, or collection of devices separate from, or in combination with BOS 255.

As shown in FIG. 7, process 700 may include receiving a notification that a transaction, associated with a user device, regarding a video asset has occurred (block 705) and retrieving information associated with a profile that corresponds to a user of the user device (block 710). For example, BOS 255 may receive a notification that user device 110, associated with a user, is associated with a transaction to obtain a video asset. The transaction may be associated with user device 110 purchasing, renting, subscribing to, etc. the video asset. Additionally, or alternatively, the transaction may be associated with an expiring license corresponding to a video asset obtained by user device 110, a content marker that identifies a point at which the video asset stopped being played by user device 110, etc.

In one example, BOS 255 may receive the notification, from IMG server 220, indicating that a set top box user device 110, associated with the user, has obtained the video asset as a result of the transaction. In another example, BOS 255 may receive the notification, from application server 215, indicating that a different type of user device 110 (e.g., a computer user device 110, a wireless handheld device 110, a gaming user device 110, etc.), associated with the user, has obtained the video asset as a result of the transaction.

BOS 255 may, in response to the notification, communicate with profile server 245 to retrieve information associated with a profile, that corresponds to the user. The information, associated with the profile (e.g., such as, all or a portion of information stored in data structure 600 of FIG. 6), may identify another user device 110 that is associated with the user.

As also shown in FIG. 7, process 700 may include identifying one or more transaction histories that correspond to the user device and/or another user device based on the information associated with the profile (block 715). For example, BOS 255 may obtain, from the information associated with the profile, information associated with one or more transaction histories, stored in IMG server 220 and/or application server 215, that correspond to the user device 110 and/or the other user device 110. In one example, a first transaction history, that is stored in IMG server 220, may correspond to a set top box user device 110 associated with the user. In another example, a second transaction history, that is stored in application server 215, may correspond to a computer user device 110 associated with the user, In a further example, a third transaction history, that is stored in application server 215, may correspond to a wireless handheld user device 110 associated with the user. Additionally, the information associated with the transaction history, may include a storage location, within the identified catalog, that stores metadata associated with video assets obtained by user device 110 and/or that are available to be accessed by user device 110.

As yet further shown in FIG. 7, process 700 may include synchronizing information that is stored in the one or more transaction histories and/or the profile that correspond to the user device (block 720). For example, BOS 255 may cause metadata, associated with the video asset, to be stored in one or more transaction histories (e.g., hosted by application server 215, IMG server 220, etc.) that corresponds to user device 110, associated with a user, with which the transaction was performed and/or one or more other user devices 110 associated with the user. Assume, for example, that the set top box user device 110, associated with the user, obtained the video asset as a result of the transaction. BOS 255 may, for example, instruct IMG server 220 to store the metadata in the first transaction history associated with the set top box user device 110, that indicates that the video asset has been obtained by the set top box user device 110. BOS 255 may, in another example, instruct catalog server 235-1 to store the metadata, associated with the video asset, in the second transaction history associated with the computer user device 110, that indicates that the video asset has been obtained by the set top box user device 110. In yet another example, BOS 255 may instruct catalog server 235-2 to store the metadata in a third transaction history (e.g., hosted by application server 215), associated with the wireless handheld user device 110, that indicates that the video asset has been obtained by the set top box user device 110. Storing the metadata in each of the transaction histories may enable another user device 110 (e.g., a type of user device 110 that is not the set top box user device 110), associated with the user, to select the metadata associated with the video asset. The other user device 110 may, by selecting the metadata, obtain the video asset without purchasing, renting, subscribing to, etc. the video asset.

BOS 255 may also send information, associated with the transaction, to profile server 245 to be stored in the profile associated with the user. In another example, BOS 255 may instruct profile server 245 to communicate with application server 215 and/or IMG server 220 to obtain information associated with one or more transaction histories (e.g., the first, second and/or third transaction histories) to be stored in the profile associated with the user. The information, associated with the transaction, may include information associate with the video asset (e.g., a title, an identifier, etc.) and/or an indication that the video asset was purchased, rented, subscribed to, etc. by user device 110.

In another example, the information associated with the transaction may include a content marker that identifies a point, associated with the video asset, at which user device 110 stopped playing the video asset. BOS 245 may instruct profile server 245 to store the content marker in the other catalog and/or the profile. Storing the content marker in the other catalog and/or the profile may allow another user device 110, associated with the user, to obtain the content marker from the user profile. Obtaining the content marker may allow the other user device 110 to play the video asset from another point that corresponds to the point at which user device 110 stopped playing the video asset.

Figure 8:
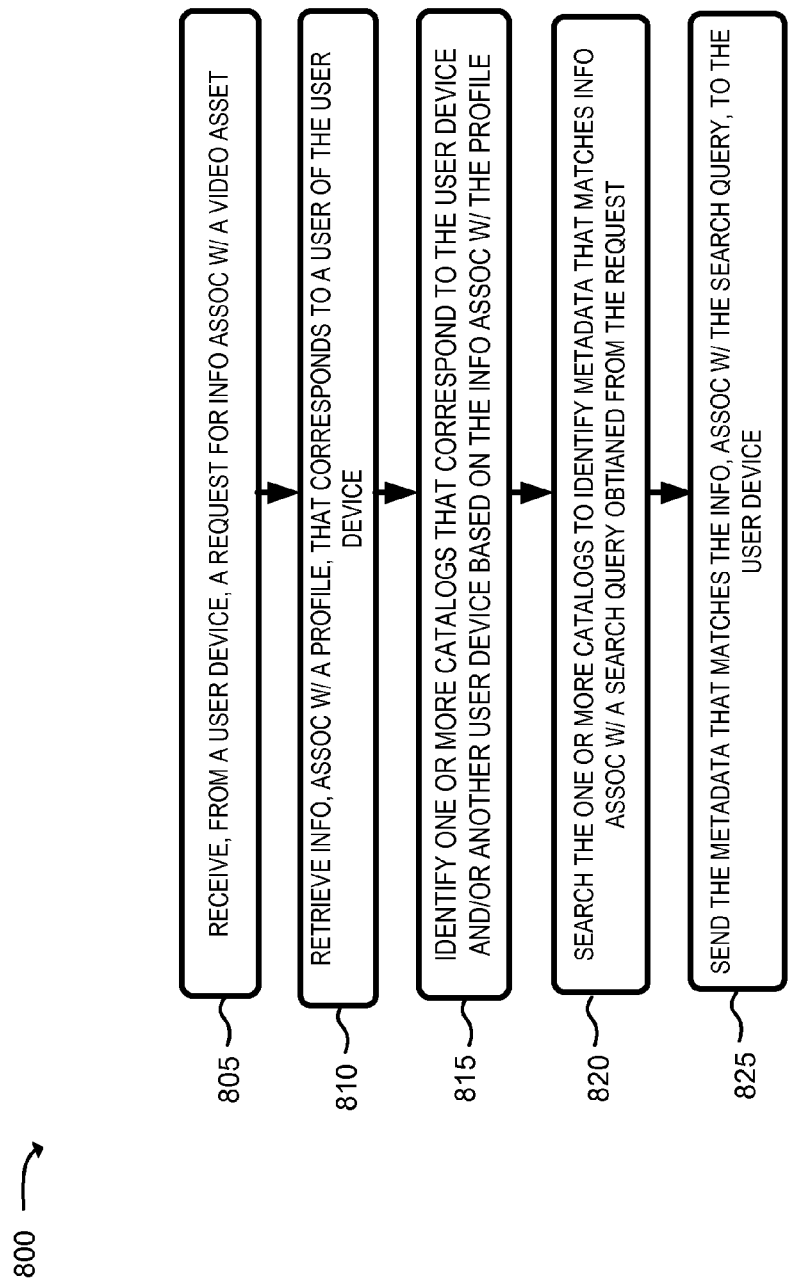
FIG. 8 is a flow chart of an example process for performing a unified search of one or more catalogs associated with the video provisioning system.

FIG. 8 is a flow chart of an example process 800 for performing a search of one or more catalogs associated with VPS 120. In an example implementation, process 800 may be performed by BOS 255. In another example implementation, some or all of process 800 may be performed by a device, or collection of devices separate from, or in combination with BOS 255.

As shown in FIG. 8, process 800 may include receiving, from a user device, a request for information associated with a video asset (block 805) and retrieving information, associated with a profile, that corresponds to a user of the user device (block 810). For example, BOS 255 may receive a request, for metadata associated with a video asset, from user device 110, associated with a user and via application server 215. The request may be associated with a search query that includes one or more key words associated with the video asset. BOS 255 may, in response to the request, communicate with profile server 245 to obtain information associated with a profile that corresponds to user device 110. The information, associated with the profile, may identify another user device 110 that is associated with the user.

As also shown in FIG. 8, process 800 may include identifying one or more catalogs that correspond to the user device and/or another user device based on the information associated with the profile (block 815). For example, BOS 255 may obtain, from the information associated with the profile, information associated with one or more catalogs, stored in IMG server 220 and/or catalog server 235, that correspond to user device 110 and/or the other user device 110. In one example, a first catalog, that is stored in IMG server 220, may correspond to a set top box user device 110 associated with the user. In another example, a second catalog, that is stored in catalog server 235, may correspond to another user device 110, associated with the user, that is a different type of user device 110 than the set top box user device 110 (e.g., a computer user device 110, a wireless handheld user device 110, a gaming user device 110, etc.).

As further shown by FIG. 8, process 800 may include searching the one or more catalogs to identify metadata that matches information associated with a search query obtained from the request (block 820) and/or sending the metadata, associated with the video asset. For example, BOS 255 may communicate with the first catalog that corresponds to the set top box user device 110 and/or the second catalog that corresponds to the other user device 110 to perform a search using the information associated with the search query (e.g., that includes the one or more key words) obtained from the request. BOS 255 may search the first catalog and/or the second catalog to determine whether information associated with the search query, matches any of the metadata stored in the first catalog or the second catalog. BOS 255 may, for example, communicate with IMG server 220 to perform the search of the first catalog. In this example, IMG server 220 may identify metadata that matches the information associated with the search query. IMG server 220 may send the metadata to BOS 255.

BOS 255 may communicate with catalog server 235 to perform the search of the second catalog. In this example, catalog server 235 may identify other metadata that matches the information associated with the search query. Catalog server 235 may send the other metadata to BOS 255.

BOS 255 may receive the metadata and/or the other metadata and may send the metadata and/or the other metadata to user device 110. User device 110 may receive the metadata and/or the other metadata and may display the metadata and/or the other metadata. The metadata may notify the user that a video asset, associated with the metadata, may be obtained from VPS 120 (e.g., via IMG 220) using set top box user device 110. The other metadata may notify the user that another video asset may be obtained from VPS 120 (e.g., via application server 215) using the other user device 110.

FIG. 9 is a flow chart of an example process 900 for distributing a video asset to one or more types of user device 110 using VPS 120. In an example implementation, process 900 may be performed by BOS 255. In another example implementation, some or all of process 900 may be performed by a device, or collection of devices separate from, or in combination with BOS 255.

As shown in FIG. 9, process 900 may include receiving, from a user device, a request for a video asset (block 905) and retrieving information, associated with a profile, that corresponds to a user of the user device (block 910). For example, BOS 255 may receive, from user device 110 and via application server 215, a request for a video asset. The request may include metadata, associated with the video asset, that identifies a genre (e.g., drama, horror, science fiction, adult, etc.), a rating (e.g., general audience (G), parental guidance (PG), restricted (R), etc.), a category (e.g., on-demand video, free broadcast video, music videos, on-line video, games, etc.) etc. associated with the video asset. BOS 255 may, in response to the request, communicate with profile server 245 to obtain information associated with a profile that corresponds to a user of user device 110.

As also shown in FIG. 9, process 900 may include obtaining, from the information associated with the profile, information associated with parental controls that are specified by a user of user device 110 (block 915). For example, BOS 255 may obtain, from the information associated with the profile, information associated with parental controls that correspond to user device 110 and/or information associated with other parental controls that correspond to another user device 110, that is associated with the user. The information, associated with the parental controls, may identify a first genre, rating, and/or category that is not authorized to be accessed, obtained, and/or played by user device 110. The information, associated with the other parental controls, may identify a second genre, rating, and/or category that is not authorized to be accessed, obtained, and/or played by the other user device 110.

In another example, BOS 255 may obtain, from the information associated with the profile, information associated with global parental controls that correspond to user device 110 and/or the other user device 110. The information, associated with the global parental controls, may identify a third genre, rating, and/or category that is not authorized to be accessed, obtained, and/or played by user device 110 and/or the other user device 110.

As further shown in FIG. 9, process 900 may include identifying to which user device 110 is the video asset to be distributed based on the parental controls (block 920). For example, the parental controls may indicate that a video asset, associated with a horror genre, is not authorized to be accessed, obtained, and/or played on user device 110. In another example, the other parental controls may indicate that a video asset, associated with a PG rating, is not authorized to be accessed, obtained, and/or played on the other user device 110. In a further example, the global parental controls may indicate that a video asset, associated with an adult genre and/or an R rating is not authorized to be accessed, obtained, and/or played on user device 110 and/or the other user device 110. Based on the parental controls and/or the global parental controls, user device 110 may not be authorized to access, obtain, and/or play a video asset associated with a horror and/or adult genre, and/or a R rating. Based on the other parental controls and/or the global parental controls, the other user device 110 may not be authorized to access, obtain, and/or play a video asset associated with an adult genre, and/or a PG and/or R rating.

BOS 255 and may identify user device 110 and/or the other user device 110 that is authorized to access, obtain, and/or play the video asset if the genre, rating, and/or category, associated with the retrieved video asset is authorized by the information associated with the parental controls, the other parental controls, and/or the global parental controls.

As further shown in FIG. 9, if the video asset is a live video asset (block 925—YES) and if a copy of the video asset is not stored in the video provisioning system (block 930—NO), then process 900 may include permitting the live video asset to be distributed, to the identified user device, by a content provider (block 935). For example, BOS 255 may communicate with IMG server 220 and/or application server 215 to determine whether user device 110 and/or the other user device 110 is to obtain the video asset, as a live video asset, from content provider 130. Additionally, or alternatively, BOS 255 may communicate with content provider 130 and/or service provider network 140 to determine whether the video asset is being broadcast, as a live video asset. Based on a determination that the video asset is to be obtained and/or is being broadcast as a live video asset, BOS 255 may communicate with VOD server 225 and/or CDN server 230 to determine whether a copy of the video asset is stored in a memory associated with VOD server 225 and/or CDN server 230. Based on a determination that the video asset is not stored by VOD server 225 and/or CDN server 230, BOS 255 may permit the live video asset to be transmitted, by content provider 130, to the identified user device 110 and/or the other user device 110.

As yet further shown in FIG. 9, if the video asset is not a live video asset (block 925—NO), or if the video asset is a live video asset (block 925—YES) and if a copy of the video asset is stored in the video provisioning system (block 930—YES), then process 900 may include transmitting the copy of the video asset to the identified user device (block 940). For example, based the communication with IMG server 220 and/or application server 215, BOS 255 may determine that user device 110 and/or the other user device 110 is not to obtain the video asset, as a live video asset, from content provider 130. Additionally, or alternatively, BOS 255 determine that the video asset is not being broadcast, as a live video asset based on a communication with content provider 130 and/or service provider network 140. Based on a determination that the video asset is not being obtained and/or broadcast as a live video asset, BOS 255 may instruct VOD server 225 and/or CDN server 230 to transmit a copy of the video asset to the identified user device 110. In one example, if the identified user device 110 is a set top box user device 110, BOS 255 may instruct VOD server 225 to transmit the copy of the video asset to the set top box user device 110. In another example, if the identified user device 110 is a different type of user device 110 than the set top box user device 110, BOS 255 may instruct CDN server 230 to transmit the copy of the video asset to the different type of user device 110.

In another example, BOS 255 may determine that video asset is being broadcast as the live video asset and may communicate with VOD server 225 and/or CDN server 230 to determine whether a copy of the video asset is being stored by VOD server 225 and/or CDN server 230. Based on a determination that the video asset is stored by VOD server 225 and/or CDN server 230, BOS 255 may, in the manner described above, instruct VOD server 225 and/or CDN server 230 to transmit the copy of the video asset to the identified user device 110.

Systems and/or methods, described herein, may enable a synchronization operation to be performed on one or more devices, associated with a VPS, to ensure that each of the devices, that distribute video assets to different types of user devices, store the same video assets. Ensuring that each of the devices store the same video assets, may allow a set top box to obtain the same video assets as another user device that is a different type of user devices than the set top box.

The systems and/or methods may enable a video asset, that is no longer available for distribution to the user devices, to be stored in the devices when the video asset has been purchased, at a prior time, by at least one of the user devices.

The systems and/or methods may that enable a transaction history and/or a profile, associated with a user, to include information regarding transactions corresponding to a set top box associated with the user and/or other transactions corresponding to the other user device, associated with the user.

The foregoing description provides illustration and description, but is not intended to be exhaustive or to limit the implementations to the precise form disclosed. Modifications and variations are possible in light of the above teachings or may be acquired from practice of the embodiments.

While series of blocks have been described with respect to FIGS. 5 and 7-9, the order of the blocks may be modified in other implementations. Further, non-dependent blocks may be performed in parallel.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/"comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act, or instruction used in the present application should be construed as critical or essential to the embodiments unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method comprising:
receiving, by a server device associated with a video provisioning system (VPS), an instruction to synchronize a first device, associated with the VPS and a second device, associated with the VPS, where the first device distributes video assets to a set top box, and where the second device distributes the video assets to another user device that is a different type of device than the set top box;
obtaining, by the server device, a first list of the video assets that are stored in a first format in the first device;
obtaining, by the server device, a second list of the video assets that are stored in a second format in the second device;
determining, by the server device, whether the first list matches the second list;
identifying, by the server device, a video asset that is not stored in one of the first device or the second device based on a determination that the first list does not match the second list; and
causing, by the server device, a copy of the identified video asset to be stored in the one of the first device or the second device.

2. The method of claim 1, where the instruction to synchronize the first device and the second device is triggered based on:
when a period of time since a previous synchronization operation was performed is greater than a time interval, or
when a current time matches a time predetermined by the server device.

3. The method of claim 1, further comprising:
storing metadata, associated with the identified video asset, in one of a first catalog, that corresponds to the first device, or a second catalog, that corresponds to the second device, where storing the metadata in the one of the first catalog or the second catalog allows the set top box or the other user device to access the metadata to obtain the identified video asset.

4. The method of claim 1, further comprising:
receiving, from the set top box, a request for another video asset;
instructing, in response to the request, the first device to transmit the other video asset to the set top box; and
storing an indication in a transaction history, corresponding to the set top box, that indicates that the other video asset was transmitted to the set top box.

5. The method of claim 4, further comprising:
storing another indication in a user profile, associated with a user of the set top box and the other user device, that indicates that the other video asset was transmitted to the set top box, where storing the other indication, in the user profile, allows the other user device to obtain the other video asset at no additional cost.

6. The method of claim 1, further comprising:
receiving, from the set top box, an indication that the video asset was obtained by the set top box, where the indication includes a content marker, the content marker identifying a point, associated with the video asset that the set top box stopped playing the video asset; and
storing the indication in a user profile associated with a user of the set top box and the other user device.

7. The method of claim 6, further comprising:
receiving, from the other user device, another request for the video asset;
retrieving, from the user profile, the indication that the video asset was obtained by the set top box; and
instructing the second device to transmit the video asset and the indication to the other user device based on the indication that the video asset was obtained by the set top box, where the instruction to transmit the video asset and the indication allows the other user device to play the video asset from the point that the set top box stopped playing the video asset.

8. The method of claim 1, further comprising:
determining that one or more of the video assets, included in the first list or the second list, are not available for distribution to one or more user devices; and
instructing the first device or the second device to delete the one or more video assets based on the determination that the one or more video assets are not available for distribution to one or more user devices.

9. The method of claim 8, where determining that the one or more of the video assets that are not available for distribution to the one or more user devices further includes:

retrieving, from a third device associated with the VPS, first metadata associated with video assets identified by the first list of video assets;

retrieving, from a fourth device associated with the VPS, second metadata associated with video assets identified by the second list of video assets;

obtaining, from the first metadata or the second metadata, a plurality of time periods of availability for the video assets identified by the first list or the second list, where the plurality of time periods of availability indicate when the video assets can be distributed to the one or more user devices; and determining that the one or more video assets, included in the first list or the second list, are not available for distribution to the one or more user devices, when a current time is not within one or more time periods, of the plurality of time periods, that correspond to the one or more video assets.

10. The method of claim 9, further comprising:

instructing the third device to remove the first metadata, from a first catalog associated with the third device, based on the determination that the one or more video assets are not available for distribution to one or more user devices; and instructing the fourth device to remove the second metadata, from a second catalog associated with the fourth device, based on the determination that the one or more video assets are not available for distribution to one or more user devices.

11. A server device, comprising:
one or more processors to:
receive, from a set top box associated with a user, a request for a video asset,
retrieve, in response to the request, a profile associated with the user, where the profile identifies another user device, associated with the user, that is a different type of user device than the set top box,
identify a first transaction history associated with the set top box, wherein the first transaction history is associated with the user and includes video assets that are stored in a first format in a first device,
identify a second transaction history associated with the other user device, wherein the second transaction history is associated with the user and includes video assets that are stored in a second format in a second device and wherein the second format is different from the first format,
synchronize the first transaction history and the second transaction history to form a synchronized transaction history,
determine whether the synchronized transaction history includes an indication that the video asset is authorized to be transmitted to the set top box,
instruct a device to transmit the video asset to the set top box based on a determination that the synchronized transaction history includes the indication that the video asset is authorized be transmitted to the set top box,
perform a transaction on the video asset that allows the video asset to be authorized to be transmitted to the set top box based on a determination that the synchronized transaction history does not include the indication that the video asset is authorized to be transmitted to the set top box, and
instruct the device to transmit the video asset to the set top box as a result of the transaction performed on the video asset.

12. The server device of claim 11, where, when determining whether the synchronized transaction history includes the indication that the video asset is authorized to be transmitted to the set top box, the one or more processors are further to:
determine whether the first transaction history identifies that a user associated with the set top box previously purchased the video asset, or
determine whether the first transaction history indicates that a period, during which the user associated with the set top box rented or subscribed to the video asset, has expired.

13. The server device of claim 11, where, when determining whether the synchronized transaction history includes the indication that the video asset is authorized to be transmitted to the set top box, the one or more processors are further to:
determine whether the second transaction history identifies that a user associated with the other user device previously purchased the video asset, or
determine whether the second transaction history indicates that a period, during which the user associated with the other user device has rented or subscribed to the video asset, has expired.

14. The server device of claim 11, where, when instructing the device to transmit the video asset to the set top box, the one or more processors are further to:
determine that the second transaction history indicates at least one of:
that the user associated with the other user device has previously purchased the video asset, or
that a period during which the user associated with the other user device rented or subscribed to the video asset has not expired.

15. The server device of claim 11, where, when instructing the device to transmit the video asset to the set top box, the one or more processors are further to:
store an indication, in the first transaction history or the second transaction history, that indicates that the video asset was transmitted to the set top box.

16. The server device of claim 11, where, when performing the transaction on the video asset that allows the video asset to be authorized to be transmitted to the set top box, the one or more processors are further to:
notify the set top box that the video asset is to be purchased, rented, or subscribed to before the video asset can be obtained by the set top box.

17. The server device of claim 16, where the one or more processors are further to:
receive an indication that the set top box obtained the video asset as a result of a transaction to purchase, rent, or subscribe to the video asset, and
store, in the first transaction history or the second transaction history, information that indicates that the video asset was purchased, rented, or subscribed to by the set top box.

18. The server device of claim 11, where the one or more processors are further to:
receive, from the set top box, a content marker that identifies a point, associated with the video asset, that the set top box stopped playing the video asset, and
store the content marker in the profile associated with the user, where storing the content marker in the profile, enables another set top box, associated with the user, to play the video asset from the point that the set top box stopped playing the video asset.

19. The server device of claim 11, where the one or more processors are further to:

receive, from the set top box, a content marker that identifies a point, associated with an other video asset, that the set top box stopped playing the other video asset, and store the content marker in the profile, where storing the content marker in the profile, enables the other user device to play a copy of the other video asset from another point that corresponds to the point that the set top box stopped playing the other video asset.

20. A system comprising:

one or more devices to:

receive an indication that a set top box, associated with a user, has obtained a video asset as a result of a transaction associated with the video asset, wherein the video asset contains video information that can be processed by the set top box, retrieve a profile, associated with the user, as a result of receiving the indication, where the profile identifies another user device, associated with the user, that is a different type of user device than the set top box, retrieve metadata, associated with the video asset, that identifies the video asset, and store the metadata or the information associated with the transaction in a first transaction history, associated with the set top box, wherein the first transaction history is associated with the user and includes video assets that are stored in a first format in a first device or a second transaction history, associated with the other user device, wherein the second transaction history is associated with the user and includes video assets that are stored in a second format in a second device and wherein the second format is different from the first format, where storing the metadata or the information associated with the transaction indicates that the video asset was obtained by the set top box as the result of the transaction, and where storing the metadata in the first transaction history or in the second transaction history permits the set top box or the other user device to access the metadata to obtain the video asset without performing the transaction;

a first server device to transmit video assets to the set top box; and a second server device to transmit the video assets to the other user device; and wherein the one or more devices are further to:

obtain a first list of the video assets that are stored in a first format in the first server device, obtain a second list of the video assets that are stored in a second format in the second server device, wherein the second format is different from the first format, determine whether the first list matches the second list, identify a particular video asset that is not stored in one of the first server device or the second server device based on a determination that the first list does not match the second list, and store a copy of the particular video asset in the one of the first server device or the second server device.

21. The system of claim 20, where the information associated with the transaction identifies at least one of:

that the video asset was purchased by a user associated with the set top box, that the video asset was rented or subscribed to by the user associated with the set top box, or a period of time associated with the video asset that was rented or subscribed to by the user associated with the set top box.

22. The system of claim 20, where the one or more devices are further to:

receive, from the other user device, a request for another video asset, retrieve, from the first transaction history or the second transaction history, other metadata associated with the other video asset or information associated with another transaction, determine, from the other metadata or the information associated with the other transaction, that the video asset has been previously transmitted to the set top box, or the other user device as a result of the other transaction, and transmit the other video asset to the other user device based on a determination that the information associated with the other transaction indicates that the other video asset was:

purchased by the user associated with the set top box or the other user device, or rented or subscribed to, by the user associated with the set top box or the other user device, for period of time that has not expired.

23. The system of claim 20, where the other user device includes at least one of:

a computer device, a tablet computer, a wireless handset device, or a gaming device.

* * * * *